United States Patent

Herrick

[11] Patent Number: 6,149,684
[45] Date of Patent: *Nov. 21, 2000

[54] PUNCTUM PLUG HAVING A THIN ELONGATED LIP AND A DISTAL STARTING TIP AND METHOD OF USING

[76] Inventor: Robert S. Herrick, 5715 N. Sycamore Ave., Rialto, Calif. 92377

[*] Notice: This patent is subject to a terminal disclaimer.

[21] Appl. No.: 08/951,690

[22] Filed: Oct. 16, 1997

Related U.S. Application Data

[63] Continuation-in-part of application No. 08/475,548, Jun. 7, 1995, Pat. No. 5,723,005.
[51] Int. Cl.⁷ .................................................. A61F 2/14
[52] U.S. Cl. ................................................. 623/4.1; 604/8
[58] Field of Search ............................. 128/887; 604/8, 604/285, 294; 623/4.1

[56] References Cited

U.S. PATENT DOCUMENTS

| | | |
|---|---|---|
| 3,949,750 | 4/1976 | Freeman . |
| 4,461,295 | 7/1984 | Herrick . |
| 4,660,546 | 4/1987 | Herrick et al. . |
| 4,915,684 | 4/1990 | MacKeen et al. ........................... 604/8 |
| 4,959,048 | 9/1990 | Seder et al. ................................. 604/9 |
| 5,049,142 | 9/1991 | Herrick et al. ........................... 604/294 |
| 5,053,030 | 10/1991 | Herrick et al. ........................ 604/890.1 |
| 5,163,959 | 11/1992 | Herrick ..................................... 623/11 |
| 5,171,270 | 12/1992 | Herrick ..................................... 623/11 |
| 5,282,063 | 1/1994 | Deacon et al. ........................... 424/427 |
| 5,318,513 | 6/1994 | Leib et al. .................................. 604/8 |
| 5,417,651 | 5/1995 | Guena et al. .............................. 604/8 |
| 5,423,777 | 6/1995 | Tajiri et al. .............................. 604/294 |
| 5,437,625 | 8/1995 | Kurihashi ................................... 604/8 |
| 5,466,258 | 11/1995 | Rubin ......................................... 623/4 |
| 5,830,171 | 11/1998 | Wallace ...................................... 604/8 |
| 5,868,697 | 2/1999 | Richter et al. ............................. 604/8 |
| 6,016,806 | 1/2000 | Webb ...................................... 128/846 |

*Primary Examiner*—Mickey Yu
*Assistant Examiner*—Tram A. Nguyen

[57] ABSTRACT

A punctum plug adapted to be inserted into the punctum opening of an eye and into the horizontal sac portion of the horizontal canaliculus is shown. The punctum plug, or implant, comprises an elongated member having a pair of ends wherein one of the pair of ends includes a collapsible flared section, or internal retaining member, which has a sloped or curved outer surface. The other end of the pair of ends includes a thin elongated lip, or external retaining member, to engage the edge of the punctum opening. The elongated member and collapsible flared section are formed of a dimension to pass through the punctum opening of an eye. The collapsible flared section has an extended position and a collapsed position. As the collapsible flared section passes through the punctum opening and into the section of the canaliculus located between the punctum opening and the ampula or horizontal sac, a clamping force is developed to collapse the collapsible flared section. The collapsible flared section passes into the ampula and reverts back to its substantially extended position. A method for treating external eye condition utilizing the punctum plug is also shown.

43 Claims, 8 Drawing Sheets

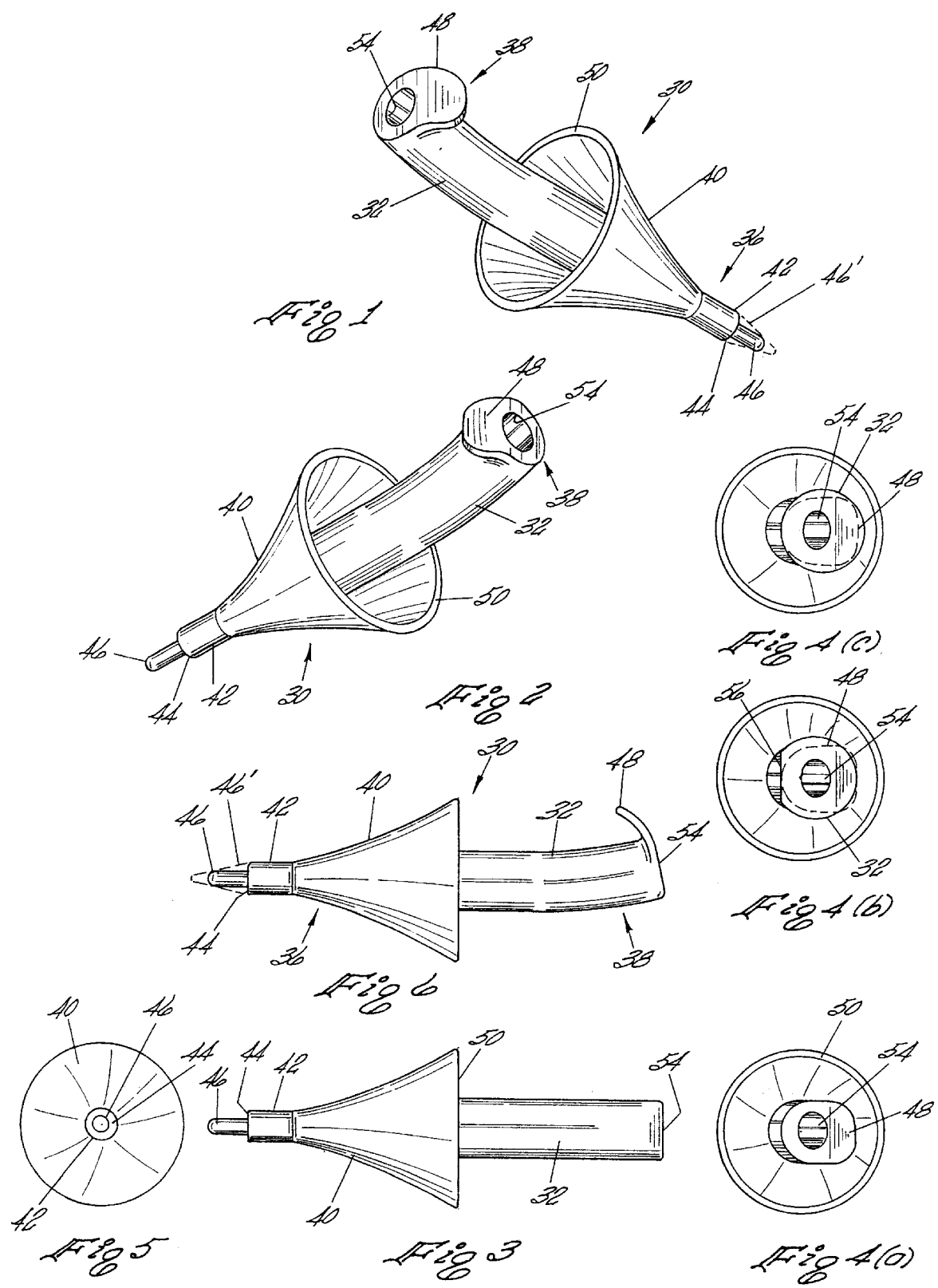

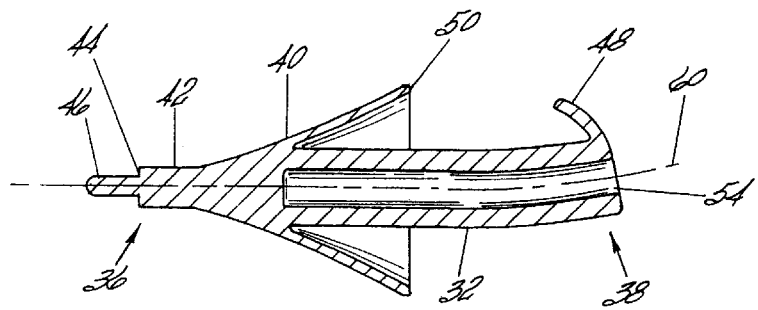
Fig 7
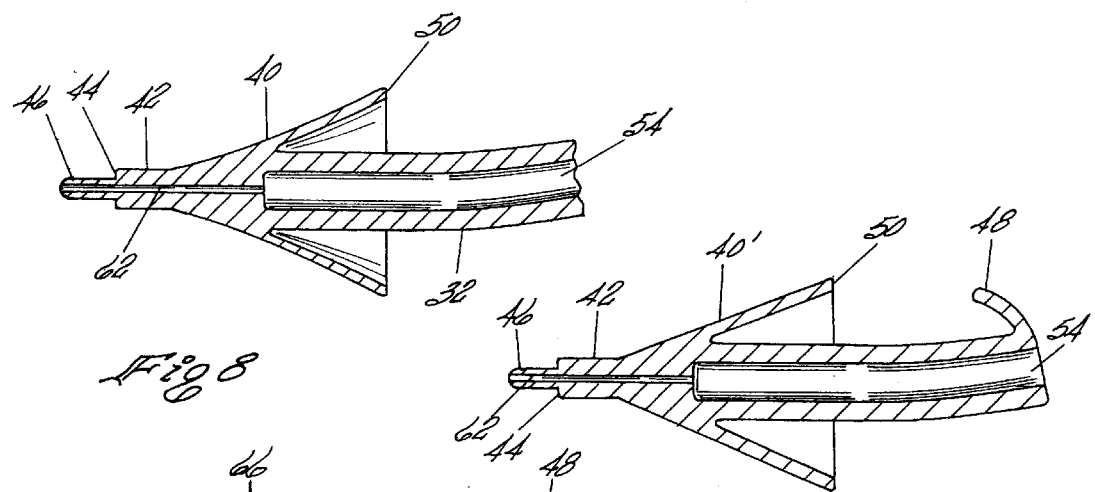
Fig 8
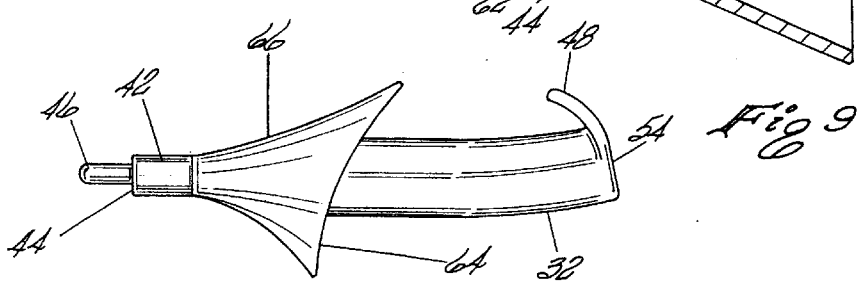
Fig 9
Fig 10
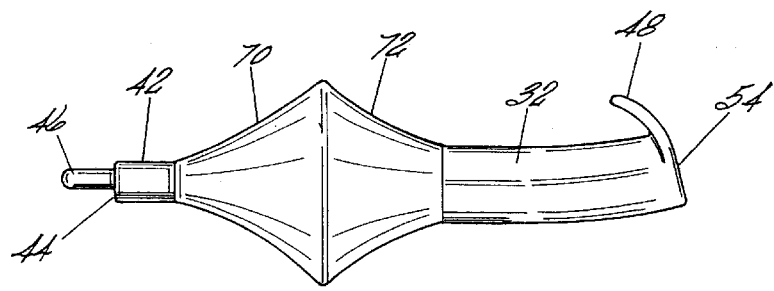
Fig 11

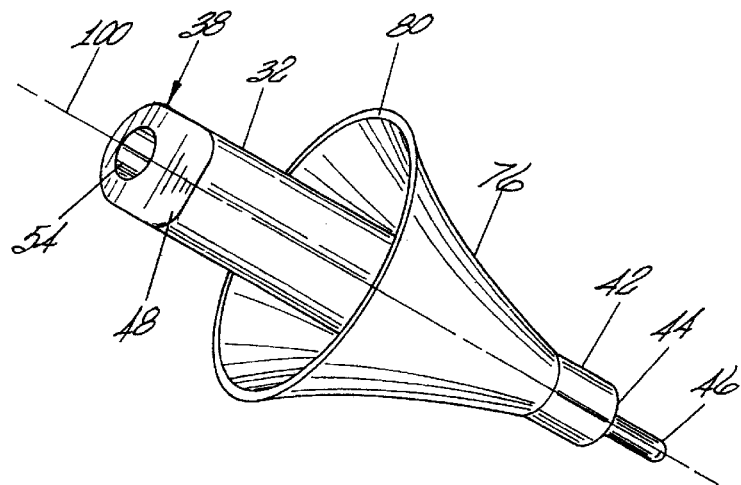
Fig 12
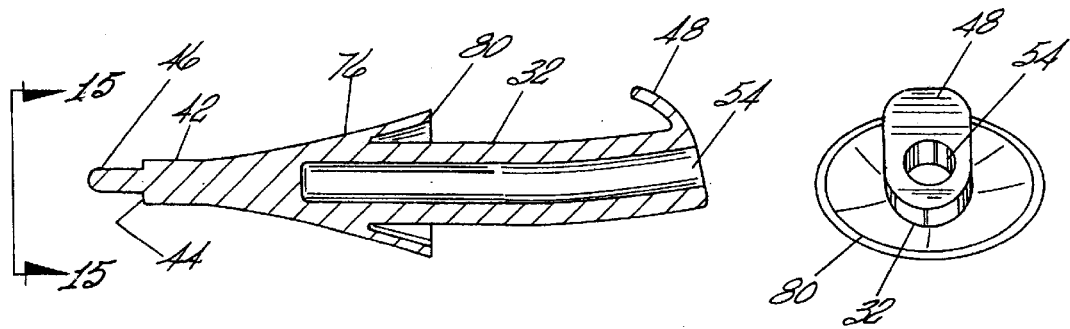
Fig 13
Fig 14
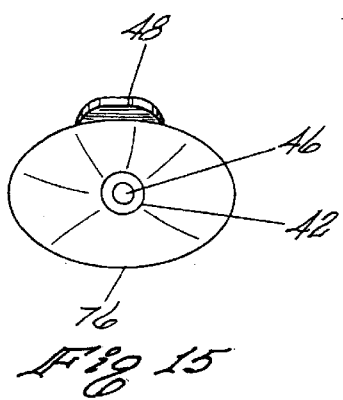
Fig 15

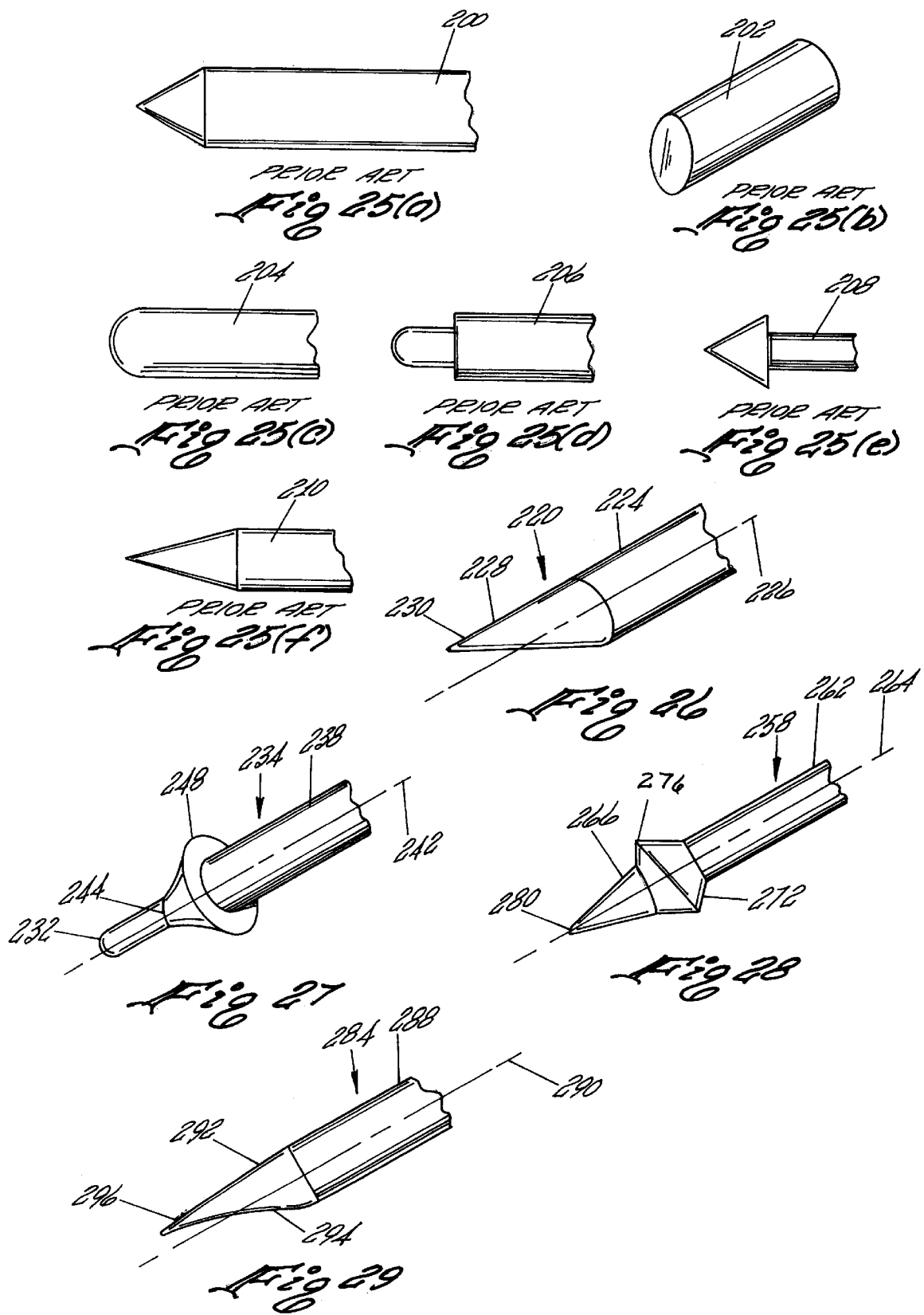

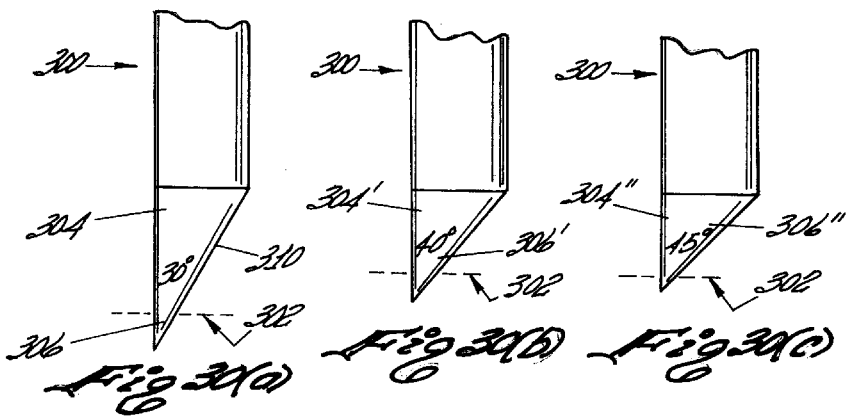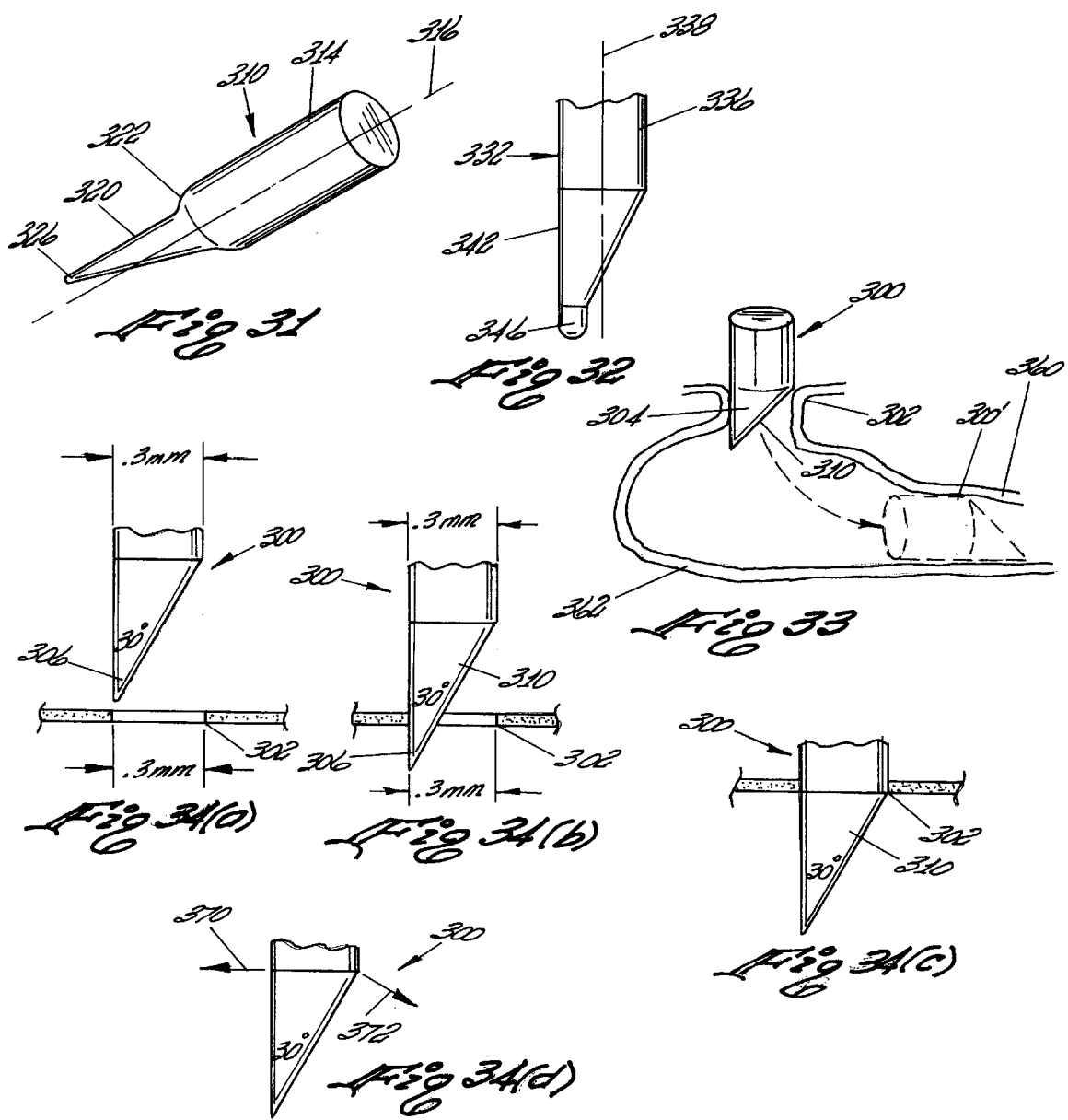

PUNCTUM PLUG HAVING A THIN ELONGATED LIP AND A DISTAL STARTING TIP AND METHOD OF USING

RELATED APPLICATIONS

This Application is a Continuation-in-Part of U.S. patent application Ser. No. 08/475,548, now U.S. Pat. No. 5,723,005, filed Jun. 7, 1995.

BACKGROUND OF THE INVENTION

1. Field of the Invention

This invention relates to a punctum plug adapted to be utilized in the treatment of a human eye having a deficiency of tears and more specifically relates to a punctum plug or implant having an elongated member having means defining a collapsed flared section at one end thereof and a thin elongated retaining tip at the other end thereof. The elongated member and the collapsible flared section are dimensional to pass through the punctum of an eye.

This invention also relates to a method for treating external eye conditions due to a deficiency of tears utilizing the punctum plug or implant having a collapsible flared section at one end thereof.

2. Description of the Prior Art

It is known in the art that certain eye problems are related to the volume of tears on the surface of the eyes. Certain of these problems include dry eyes, corneal ulcer, conjunctivitis, blepharitis, contact lens problems and many other external eye diseases.

One method for treating for a deficiency of tears is disclosed in U.S. Pat. No. 4,660,546, wherein the inventor is the same inventor of the present invention. U.S. Pat. No. 4,660,546 discloses a method for treating external human eye conditions due to a deficiency of tears which includes the step of temporarily blockading the canaliculus of the patient and observing over a preselected period of time the response of the patient's eye to the temporary blockage and to determine if any improvement in the eye condition has been achieved in response to the occlusion. If an improvement in eye condition is noted, an implant is placed within the horizontal portion of at least one of the canaliculi of the patient. A temporary blockading of the canaliculus is performed by placing a dissolvable, removable element, which may be in the form of a collagen material or other dissolvable material such as, for example, catgut, in the canaliculus. Unless removed shortly after insertion, the dissolvable implant is hydrolyzed by the body fluid in approximately a one to two week period. A determination is first made if the canaliculus blockage results in an improvement in the eye condition or other conditions caused by related non-allergic nasal congestion warranting permanent blockage of the canaliculus, for example, the patient will respond to a partial 60% to 80% retention of constant tears. If permanent partial blockage of the canaliculus is warranted, U.S. Pat. No. 4,660,546 discloses that the permanent blocking of the canaliculus is performed by utilizing a permanent implant. U.S. Pat. No. 4,660,546 discloses that the permanent implant is fabricated of a nonabsorbable or non-dissolvable material and is in the form of a cylindrically shaped central body having a tapered end or an end of reduced diameter to facilitate the implantation of the implant into and for removal of the implant from the canaliculus. Both the temporary collagen implant or other dissolvable material and the permanent implant disclosed in U.S. Pat. No. 4,660,546 are in the form of a cylindrically shaped central member having a predetermined diameter which may terminate at one end in a tapered end and which reduces in diameter as it slopes away from the central member to form a tapered tip to facilitate insertion of the implant through the punctum, through vertical canaliculus and into the horizontal portion of the canaliculus.

U.S. Pat. No. 4,461,295, wherein the inventor thereof is the same as the inventor of the present invention, discloses another treatment method which is a method for laser punctal occlusion. It is known in the art that punctal occlusion has been proven to be an effective way of treating patients with conditions such as sinusitis, hay fever, middle ear infection (chronic), post nasal drip, front headache and other such conditions. The treatment method disclosed by U.S. Pat. No. 4,461,295 includes the use of a temporary suture to stitch the tear drainage canals of the eyes closed to determine if a greater tear volume on the surface of the eyes would improve certain eye problems. This diagnostic procedure has become known in the art as the Herrick Stitch Test. The Herrick Stitch Test is performed by anesthetizing the local area around the lower or upper punctum of the eye. A stitch is carefully placed to occlude the punctum by an eye surgeon utilizing magnification of the eye. After a preselected period of time using the Herrick Stitch Test, the eye surgeon determines if the eye condition has improved, if so, then the eye surgeon permanently closes the punctum by using an ARGON laser. The punctum may be reopened at a later time if excess tearing is experienced. The reopening of the punctum can be performed by surgical and laser techniques, all as disclosed in U.S. Pat. No. 4,461,295.

It is also known in the art to utilize other plugs and or techniques for occluding the punctum. One plug device which is known in the art is referred to as a punctum plug which is described in an article by Jerre M. Freeman, MD, entitled "The Punctum Plug: Evaluation of a New Treatment for the Dry Eye" which appeared in the publication of the transcripts of the America Academy of Ophthalmology and Optometry, pages OP-874 through OP-879 (hereinafter referred to as the "Freeman Reference"). In addition, the same punctum plug is disclosed and described in U.S. Pat. No. 3,949,750.

The punctum plug disclosed in the Freeman Reference and in U.S. Pat. No. 3,949,750 is a plug which is adapted to be inserted into the punctal openings of the eye to block or occlude the punctum. The punctum plug of Freeman is a rod-like plug formed with an oversized rigid or solid tip or barb portion that dilates and blockingly projects into the vertical portion of the canaliculus. The punctum plug has a smaller neck or waist portion around which the punctum sphincter ring tightens. The punctum plug has relatively large, smooth head portion which rests on top of the punctal opening and prevents the plug from passing down into the canaliculus. The smooth head portion is designed to be domed shaped to permit the head to rest in the lacrimal lake and against the conjunctiva and cornea with little irritation. The head portion functions to prevent the punctum plug from passing into the horizontal portion of the canaliculus. The punctum plug of Freeman is subject to being inadvertently removed from the eye by the patient.

It is also known in the art to provide for a temporary closure of the punctum by heat using a light cautery around and in the punctal opening. The punctal closure procedure is disclosed in an article entitled "Diagnosis and Treatment of Keratoconjunctivitis Sicca" which appeared in a symposium on medical and surgical diseases of the cornea, transactions of the New Orleans Academy of Ophthalmology in 1980 at page 43 wherein the authors thereof were Jose I. Barraquer, MD and eight other authors (hereinafter referred to as the "Barraquer Reference"). The Barraquer Reference further discloses that other treatment methods of temporarily closing the punctum include use of gelatin plugs, cyanoacrylate adhesives and diathermy. The use of intracanalicular gelatin implants for treatment of eye conditions is described in an article entitled "INTRA-CANALICULER GELATIN IMPLANTS IN THE TREATMENT OF KERATO-CONJUNCTIVITIS SICCA" by Wallace S. Foulds which appeared in the Brit J. Ophthal (1961) in Volume 45 at pages 625 through 627, inclusive, (the "Foulds Reference"). The Foulds Reference discloses that occlusion of the lacrimal puncta can be performed by use of and insertion of a fine, water soluble gelatin rod into the punctal openings. The gelatin rod is formed from pure powdered gelatin to which a small quantity of distilled water has been added and is heated in a water bath until the gelatin dissolves and a thick gel results. By dipping a cold glass rod into the so prepared gelatin, and withdrawing the same, fine solid rods of gelatin were formed. The so formed gelatin rods were then inserted into the canaliculi to provide a temporary blockage. As such, the gelatin rod implants, although very fragile, provide an alternate known means for temporarily blocking the canaliculus. If an improvement in eye condition is obtained, then permanent closure of the canaliculi may be warranted.

It is known in the art that a Schirmer's test can be utilized to measure gross tear secretion. If the results of the Schirmer tear secretion test discloses that an insufficient portion of the tear secretion is retained on the eyes, a temporary or permanent occlusion of the canaliculi may prove helpful to improving the above described external eye conditions.

An improvement over the Freeman punctum plus described in U.S. Pat. No. 3,949,750 is shown in U.S. Pat. No. 4,915,684. U.S. Pat. No. 4,915,684 discloses a lacrimal fluid modulating device composed of a generally cylindrical body portion with an enlarged cap at one inlet and a tapered peripheral enlargement at an outlet end. The tapered peripheral enlargement is solid. An axial bore extends completely through the modulating device and is fashioned with an outlet end having an internal diameter which is preferably no less than 0.12 and no greater than 0.36 mm.

A tapered shaft punctum plug for occlusion of the punctum opening having a tapered shaft and including one end that terminates in a narrow neck and a concave dome and another end that terminates in a solid pointed nose is offered for sale by Eagle Vision under the trademark SUPER PLUG.

Another punctum plug that is commercially available for occluding the punctum opening is known as an UMBRELLA PLUG. The UMBRELLA PLUG has an elongated cylindrically shaped central member having one end that is cut at an angle relative to the central axis and terminates in a flat, circular washer like cap or collarette. The UMBRELLA PLUG has at its other end a collapsible umbrella shaped bulb which is intended to collapse closing like an umbrella during insertion of the umbrella shaped bulb through the punctum and when the umbrella has passed through the punctum opening, it then reverts back to an open position.

As is evidenced by the above described prior art, the two approaches used to occlude the lacrimal drainage system are to: (a) occlude the punctum opening and vertical portion of the canaliculus, e.g., Freeman U.S. Pat. No. 3,949,750, U.S. Pat. No. 4,915,684 the SUPER PUNCTUM PLUG and the UMBRELLA PLUG; and (b) occlude the horizontal portion of the canaliculus, e.g., U.S. Pat. Nos. 4,660,546 and 5,049,142. However, other implants which can be used to occlude either the vertical portion or the horizontal portion of the canaliculus are U.S. Pat. Nos. 5,163,959 and 5,171,270 wherein the inventor thereof is the same inventor as in the present Application.

In practice, however, it has developed that the transition from the vertical portion of this canaliculus to the horizontal portion of the canaliculus does not occur as a distinct transition point, but rather occurs through an intermediary section referred to as the ampula or horizontal sac.

Therefore, an implant which occludes the punctum opening and vertical section of the canaliculus, depending on its length, can have a portion thereof located in the ampula or sac. By occluding the lacrimal drainage system in this manner, it is not necessary that the implant physically be located in the horizontal portion of the canaliculus to be effective. On the other hand, if an implant, without a dome or collarette, is inserted into the punctum opening or the vertical section of the canaliculus, that implant generally migrates through the punctum opening through the vertical section of the canaliculus, into the ampula or sac, and can easily migrate into the horizontal portion of the canaliculus.

SUMMARY OF THE PRESENT INVENTION

The present invention discloses a new, novel and unique punctum plug or implant which comprises an elongated central member having one end which terminates in a thin elongated lip, or external retaining member, which can be positioned over the edge of the punctum opening of the eye and away from the cornea. The punctum plug includes a second end having a collapsible flared section, or internal retaining member. In the preferred embodiment of the present invention, the punctum plug or implant is adapted to be inserted into the punctum opening of an eye and to be transported into the vertical portion of the canaliculus, and if of sufficient length, into the ampula of the canaliculus to occlude the punctum opening and that portion of the canaliculus extending between the punctum opening and ampula. The punctum plug includes an elongated member having a first end and a spaced, opposed second end and a central member. In the preferred embodiment, the first end is slightly angularly disposed from the second end. The second end has a collapsible flared section which terminates in an outer edge having dimension which is greater than the cross-sectional dimension of the central member. The collapsible flared section has an expanded position and a collapsed position wherein the dimension of the collapsed position is approximately equal to the geometrical dimension of the punctum opening of an eye adapted to receive the same. The application of a radial force to the collapsible flared section in a direction to collapse the outer edge thereof urges the collapsible flared section from its extended position into its collapsed position. If the length of the punctum plug is selected to keep the collapsible flared section within that portion of the canaliculus located between the punctum opening and ampula, the clamping force developed between the collapsible flared section and interior side walls of the canaliculus holds the punctum plug in place since the second end does not extend into the ampula.

If the punctum plug has sufficient length, once the collapsible flared section passes through the punctum opening and vertical portion of the canaliculus into the ampula or sac, it reverts back to its substantially extended position. The canalicular implant may be fabricated from a biodegradable material if it is to be used as a temporary implant, or may be formed of a non-biodegradable material if it is to be used as a permanent implant.

The known prior art implants for providing temporary and permanent occlusion of the punctum opening and vertical portion of the canaliculus has certain disadvantages. One disadvantage is that a temporary implant, disclosed by the prior art, may have to be removed before it has been fully dissolved or absorbed, as the case may be. If the eye surgeon is unable to remove any part of or all of the temporary implant, the portion of the temporary implant not removed must remain in the canaliculus until it ultimately is dissolved in the body thereby terminating the occlusion of the canaliculus. Typically, an eye surgeon will utilize the temporary implant as a means for determining if the permanent occlusion of the canaliculi will result in an improvement of eye conditions as described hereinbefore. It is possible for the temporary collagen implant if inserted into the punctum opening or vertical portion of the canaliculus, for example, to migrate into the horizontal portion of the canaliculus or back out of the eye or to otherwise not remain in place. Also, the temporary implants may be too fragile to remove in a single piece during removal thereof, if required, by the eye surgeon.

In addition, the insertion and use of a permanent implant having a central body and a tapered end, which is usually formed of a nonabsorbable or non-dissolvable material, can be utilized to permanently occlude either the vertical portion or the horizontal portion of the canaliculus. However, such a permanent implant can still migrate within the lacrimal system and into the horizontal portion of the canaliculus or out of the eye. Any migration of a permanent punctal implant is undesirable.

The laser treatment to obtain punctal occlusion, although quite effective, has certain disadvantages. One disadvantage is injection of a local anesthetic is required and the patient may experience some pain or discomfort for one to two days after the procedure. Also, some discharge may occur for seven to ten days. Vision may be blurred for a few days. If the patient wears contact lens, the contact lens may be uncomfortable for a few days.

The other known punctum plugs have a convex dome or collarette to act as a cap to prevent the punctum plug from migrating through the punctum opening, through the vertical portion of the canaliculus, into the ampula or sac or into the medial position of the horizontal portion of the canaliculus. Such caps are generally circular and result in an edge which engages, contacts or otherwise abrades the cornea or conjunctiva.

Therefore, one advantage of the canalicular implant of the present invention is that the punctum plug or implant, when positioned in the punctum opening of the canaliculus, will be held in place and restricted from movement by a thin elongated lip which is urged against the edge or sphincter muscle of the punctum opening and the collapsible flared section of the implant located either within that portion of the canaliculus located between the punctum opening and the ampula, or within the ampula.

Another advantage of the present invention is that the implant includes a collapsible flared section which has an outer edge which is slideably urged against the interior walls of the punctum opening during insertion and placement within the vertical portion of the canaliculus to hold the implant in position while concurrently occluding the canaliculus.

Another advantage of the present invention is that the canalicular implant is relatively easy to insert without the necessity of using an injectable anesthetic.

Another advantage of the present invention is that the permanent implant, when positioned in the punctum opening and vertical portion of the canaliculus, does not cause any tissue irritation or irritation to the eye due to migration of the same out of the canaliculus and through the punctum opening into the eye.

Another advantage of the present invention is that the punctum plug or implant is easily removable and does not cause any discomfort, does not cause any pain to the patient or irritation to the cornea or conjunctiva of the eye of a patient, there is no discharge for several days, the patient's vision is not subject to blurring for several days and, if the patient wears contact lenses, the contact lenses will not be uncomfortable for several days.

Another advantage of the present invention is that due to the holding action between the collapsible flared section of the second end of the implant and the thin elongated lip of the first end which is urged against the sphincter muscle of the punctum opening, the canalicular implant cannot be easily or readily dislodged by patient activity or movement.

Another advantage of the present invention is that the punctum plug or implant causes no long term discomfort to the user when the same is in place.

Another advantage of the present invention is that the punctum plug or implant is effective in blocking a drainage of tears through the punctum opening and the vertical portion of the canaliculi. Thus, if only a partial blockage of drainage of tears is required, the punctum plug or implant can having a fluid metering opening extending axially therethrough.

Another advantage of the present invention is the collapsible flared section of the punctum plug or implant can include a hollowed out central area which defines a thin walled, conical-shaped flared section.

Another advantage of the present invention is that the thin walled, conical-shaped flared section can terminate in an outer edge which may be circular shaped, conical shaped or other configuration.

Another advantage of the present invention is that the elongated member may have a slight angular curve to urge the thin elongated lip into engagement with the edge of the punctum opening and away from the cornea.

Another advantage of the present invention is that the collapsible flared section can be non-uniform such as being cut at a bias or having a non-circular cross-section, such as being elliptically shaped.

Another advantage of the present invention is that the collapsible flared section of the canalicular implant can include a tool receiving opening in the central section thereof which is adapted to cooperate with an insertion tool.

Another advantage of the present invention is that the cross-section diameter of the central member preferably would have a diameter of about 0.3 mm to about 1.2 mm while the outer edge of the collapsible flared section can have a diameter in the order of about 0.5 mm to about 2.2 mm. Also, the cross-section of the central member may be oval shaped with similar appropriate dimensions.

Another advantage of the present invention is that the punctum plug or implant can be formed of a nonabsorbable or non-dissolvable material such as silicone, polytetrafluoroethylene (e.g. Teflon) or other medically compatible non-biodegradable material.

Another advantage of the present invention is that the punctum plug or implant could be formed of an absorbable or dissolvable material to function as a temporary implant. One such absorbable or dissolvable material that could be utilized for practicing this invention is collagen.

Another advantage of the present invention is that the length of the punctum plug can be selected to place the collapsible flared section in the vertical portion of the canaliculus or place the collapsible flared section into the ampula.

Another advantage of the present invention is that a method for treating an external eye condition due to a deficiency of tears using the punctum plug of the present invention which can be used for treating an eye is shown.

BRIEF DESCRIPTION OF THE DRAWINGS

The foregoing and other advantages of this invention will be apparent from the following description of the preferred embodiment of the invention when considered with the illustrations and accompanying drawings which include the following Figures:

FIG. 1 is a front, top and right end perspective view of a punctum plug of the preferred embodiment having a thin elongated lip at the lateral end and a collapsible flared section at the medial end;

FIG. 2 is a bottom, rear and right end perspective view of the punctum plug of FIG. 1;

FIG. 3 is a front elevational view thereof;

FIGS. 4(a), 4(b) and 4(c) are a right side elevational view of FIG. 3; an alternate structure having a chamfered edge and an eccentric variation, respectively, to prevent the lateral end from contacting the cornea;

FIG. 5 is a left side elevational view thereof;

FIG. 6 is a bottom elevational view thereof;

FIG. 7 is a cross-sectional view of the punctum plug of FIG. 1, having tool receiving opening in the center of the collapsible flared section having uniformly sloping side walls which is adapted to cooperate with an insertion tool;

FIG. 8 is a cross-sectional view of an alternate embodiment of FIG. 7 having a fluid metering opening extending therethrough; punctum plug tool receiving opening within a collapsible flared section having curved sloping walls which is adapted to cooperate with an insertion tool;

FIG. 9 is a cross-sectional view of yet another embodiment of a punctum plug having an elongated tool receiving opening which is adapted to cooperate with an insertion tool and wherein a fluid metering opening extends through and out the medial end;

FIG. 10 is a bottom elevational view of yet another embodiment of the punctum plug wherein the collapsible flared section has curved outer walls and wherein the outer edge is cut on the bias relative to the central axis of the elongated member;

FIG. 11 is a bottom elevational view of yet another embodiment of the punctum plug wherein the collapsible flared section is formed by two conical-shaped members having curved outer walls wherein the outer edges thereof are joined to form a bellows shaped collapsible flared section;

FIG. 12 is a modification of the embodiment of FIG. 6 wherein the elongated member has a relatively straight central axis;

FIG. 13 is a cross-sectional bottom elevational view of yet another embodiment of a punctum plug having a collapsible flared section which is elliptically shaped;

FIG. 14 is a right end elevational view of FIG. 13;

FIG. 15 is a left end elevational view of FIG. 13;

FIGS. 22(a) through 22(c) are pictorial representations of the steps of insertion of a punctum plug of the present invention into the punctum opening and canaliculus wherein FIG. 22(a) illustrates the punctum plug being passed through the punctal opening; FIG. 22(b) illustrates the punctum plug passing through the vertical portion of the canaliculus; and FIG. 22(c) illustrates the collapsible being positioned within the ampula or sac.

FIGS. 25(a) through 25(f) illustrate known prior art starting tips used for punctum plugs and lacrimal implants;

FIG. 26 is a top, front and left side perspective view of a starting tip having a partially sloped surface which terminates in a distal starting tip and wherein the distal starting tip is offset relative to the elongated central axis of the elongated body;

FIG. 27 top front and right side perspective view of a starting tip having an enlarged proximal area which slopes toward a distal starting tip which is co-axial and aligned with the elongated axis of the elongated body;

FIG. 28 top, front and right side perspective view of a starting tip having an enlarged annular shaped proximal area defining a circumferentially extending outer edge which slopes toward a distal starting tip which is co-axial and aligned with the elongated axis of the elongated body;

FIG. 29 is a top, front and left side perspective view of a starting tip having a partially curved and sloped surface which terminates in a distal starting tip and wherein the distal starting tip is offset relative to the elongated central axis of the elongated body;

FIGS. 30(a), 30(b) and 30(c) illustrate various embodiments wherein the angle of the sloped surface varies as a function of the length of the distal starting tip illustrated in FIG. 26;

FIG. 31 is a top, front and left side perspective view of a starting tip having an offset partially curved and sloped surface which terminates in a distal starting tip and wherein the distal starting tip is offset relative to the elongated central axis of the elongated body;

FIG. 32 is a top, front and left side perspective view of a starting tip having a sloped surface which terminates in a distal starting tip having a rounded terminus and wherein the distal starting tip is offset relative to the elongated central axis of the elongated body;

FIG. 33 is a pictorial representation of the path traversed by an implant illustrated in FIGS. 30(a), 30(b) and 30(c) when passed through the punctum opening and into the horizontal canaliculus including the horizontal sac; and FIGS. 34(a), 34(b), 34(c) and 34(d) which illustrate the steps of a method for inserting an implant having a starting tip illustrated in FIG. 30(a) wherein the offset starting tip is used to slightly dilate the punctum opening into an oval shape during insertion.

DESCRIPTION OF THE PREFERRED EMBODIMENT

Figure 16:
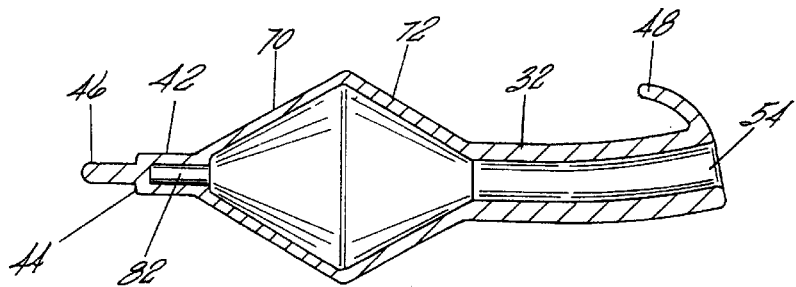
FIG. 16 is a cross-sectional bottom elevational view of yet another embodiment of a collapsible flared section in the form of a bellows defined by two conical-shaped collapsible flared sections having sloped outer walls and joined at the outer edges or outer rings.

The following description of Figs. applies generally to FIGS. 1 through 6 and uses the same reference numerals for reference to the same elements. Similar reference numerals are used in the other Figs.

As illustrated in FIGS. 1 through 6, the implant, which in the preferred embodiment is a punctum plug, is shown generally as 30 and includes an elongated member 32 having a pair of ends 36 and 38. One of the pair of ends, in the preferred embodiment the first end, 36 includes a collapsible flared section 40 having an outer surface. The other of said pair of ends, in the preferred embodiment the second end, 38 includes a thin elongated lip. The elongated member 32 and the collapsible flared section 40 is formed of a dimension to pass through a punctum opening and vertical portion of the canaliculus of an eye.

For purposes hereof, the term "thin elongated lip" means an extension or lip which extends or protrudes beyond the outer surface of the elongated member and which would be located around approximately 300° or less of the periphery of the elongated member leaving the posterior surface thereof free from protruding into, or from contacting with or from abrading the surface of the eye including the cornea or conjunctiva. This can be accomplished in any way including the embodiments disclosed herein such as FIGS. 1, 4(a), 4(b) and 4(c) which are exemplary.

In the preferred embodiment, the elongated member 32 curves slightly in a direction towards the other of said pair of ends 38. Thus, the end 38 is slightly angularly disposed relative to the one end 36. The end 36 includes a tip insert section 42 having a shoulder 44 and a distal starting tip 46 which is smaller in cross-sectional dimension than the tip insert section 42. In the alternative, the distal starting tip 46 may be a tapered end shown as 46'.

The collapsible flared section 40, is illustrated to have curved outer wall and defines a thin walled, conical shaped member which terminates in the outer edge or outer ring 50. In the embodiment in FIG. 1, the cross-section of the conical shaped collapsible flared section 40 is generally circular. The collapsible flared section 40 is located between the pair of ends 36 and 38 and is located adjacent to the first end 36.

The other end 38, or the second end, terminates in a thin elongated lip 48 which is located at a selected position on end 38. The thin elongated lip 48 is operatively connected to the lateral end 38 so as to be positioned away from the cornea when the implant has been inserted into the eye. An elongated opening 54 extends from the second end 38 to a location intermediate the conical-shaped collapsible flared section 40 and this is shown in greater detail in FIG. 7.

FIG. 4(a) illustrates one structure where the thickness of the lateral end 38 is controlled or selected to avoid contact with the cornea. FIGS. 4(b) and 4(c) illustrate two alternative structures to ensure that the lateral end 38 does not contact or abrades the cornea. Specifically, in FIG. 4(b) the lateral end 38 can have a chamfered edge 56 formed on the posterior surface thereon. The combination of a slight bend in the elongated member 32 together with the chamfered edge, eliminating any protrusion on the posterior surface, further discourages or prevents cornea or conjunctival touching. FIG. 4(c) shows that the elongated opening 54 can be eccentricity located within the elongated member 32 to cooperate with the slight angular disposition to ensure that the portion of the lateral end 38 located near the cornea does not contact or abrades the cornea. The thin elongated lip 48 is shown by dash lines on FIGS. 4(b) and 4(c).

The thin elongated lip 48 may extend beyond the body of the elongated member 32 on all but the posterior side located adjacent the surface of the eye including the cornea and conjunctiva.

FIG. 7 illustrates in a cross-sectional bottom elevational view that the elongated member 32 has a central axis 60. As is evident from the illustration in FIG. 7, second end 38 is slightly angularly disposed relative to the first end 36. FIG. 7 also shows that the elongated opening 54 terminates within the elongated member 32 at a position which is between the outer edge 50 and the first end 36. The elongated opening 54 functions as a tool receiving opening. As is apparent from the cross-sectional view of FIG. 7, the collapsible flared section 40 has curved outer walls.

FIG. 8, which is a cross-sectional bottom elevational view of another embodiment similar to FIG. 7, shows that a fluid controlled opening 62 is formed from the distal starting tip 46 through the tip insert section 44 and through the conical shaped collapsible flared section 40 into communication with the elongated opening 54. The fluid control opening 62 is used to pass or meter lacrimal fluid through the punctum plug 30. The fluid control opening 62 is selected to have a predetermined diameter to control the flow of lacrimal fluid passed therethrough. The fluid control opening can have a diameter in the range of about 0.10 mm to about 0.40 mm.

FIG. 9, which is a cross-sectional elevational bottom view of yet another embodiment of a punctum plug has a collapsible flared section 40' having sloping walls. The sloping walls in the conical flared section 40' presents a different profile than the sloping walls of the collapsible flared section 40 illustrated in FIG. 7. In FIG. 9, a fluid control opening 62, which is an alternative structure, may be formed in the punctum plug in FIG. 9. However, the fluid control opening 62 could be eliminated to form a structure which is similar to that of FIG. 7 which does not have a fluid control opening.

FIG. 10 illustrates yet another embodiment of a punctum plug wherein the collapsible flared section 64 has a non-uniform shape for enabling the collapsible flared section 64 to be collapsed relative to the central axis, such as central axis 60 illustrated in FIG. 7. In the embodiment of FIG. 10, the outer edge 66 is formed on a bias which makes the implant asymmetrical relative to the central axis of the elongated member 32. By forming an offset outer edge 66, the punctum plug can be fabricated to form a angularly shaped holding edge. FIG. 10 is illustrated to have a tip insert section 42, a shoulder 44 and distal starting tip 46 to facilitate opening of the punctum opening with less trauma and as a means for positively starting insertion of the medial end of the punctum plug 30.

FIG. 11 illustrates yet another embodiment of a punctum plug having a pair of conical shaped collapsible flared section 70 and 72 which are coaxially aligned with the central axis of the elongated member 32 and wherein the outer edges thereof are joined together to form a collapsible bellows structure. FIG. 11, in a structure similar to FIG. 10, is illustrated to have a tip insert section 42, a shoulder 44 and distal starting tip 46 to facilitate opening of the punctum opening with less trauma and as a means for positively starting insertion of the medial end of the punctum plug 30.

FIG. 12 illustrates yet another embodiment wherein the collapsible flared section 76 has two different structural features relative to the punctum plug of FIGS. 1 through 6. Specifically, the elongated member 32 is shown to be straight rather than having a slightly angular curve which is illustrated in FIGS. 1 through 6. In the embodiment of FIG. 12, the central axis 100 is straight without any angular deflection. In this structure, it may be necessary to utilize a chamfered edge as illustrated in FIG. 4(*b*) to avoid the lateral end 38 from contacting the cornea. The length of the elongated member can be selected to place the collapsible flared section within the vertical portion of the canaliculus wherein a clamping action of the collapsed collapsible flared section against the interior walls of the vertical portion of the canaliculus hold the punctum plug in place.

Also, the length of the elongated member can be selected to place the collapsible flared section within the ampula where the collapsible flared section reverts back to its substantially extended position.

Another structural difference in FIG. 12 resides in the fact that the collapsible flared section 76 has an outer edge 80 which is elliptically shaped.

Another embodiment wherein the collapsible flared section is elliptically shaped is shown in FIGS. 13 through 15. FIG. 13 shows, in cross-section, that the collapsible flared section 76 has curved outer walls and an outer edge which is elliptically shaped. FIG. 14 shows that the thin elongated lip 48, which may be a an external retaining member, is positioned normal to the major axis of the elliptically shaped outer edge 80. The elliptically shape of the collapsible flared section 76 provides a non-uniform collapsible flared section to enable the punctum plug to conform with the interior of the ampula which is located within the human eye.

FIG. 15 shows that the distal tip section 42 terminates in the distal starting tip 46 to facilitate a non-traumatic insertion of the punctum plug. In the alternative, the distal starting tip 46 can be tapered to eliminate the shoulder 44 as shown by 46' in FIG. 1.

FIG. 16 illustrates in a cross-sectional view the bellows structure shown in FIG. 11. The elongated opening 54 communicates with a hollowed-out central area located within each of the conical-shaped collapsible flared sections 70 and 72 and communicates with a remote tool receiving opening 82 located within the tip insert section 44.

Figure 17:
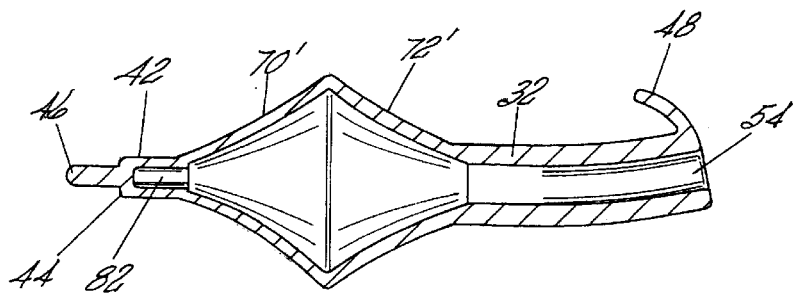
FIG. 17 is a cross-sectional bottom elevational view of yet another embodiment of a collapsible flared section in the form of a bellows defined by two conical-shaped collapsible flared sections having curved outer walls and joined at the outer edges or outer rings.
Figure 18A:
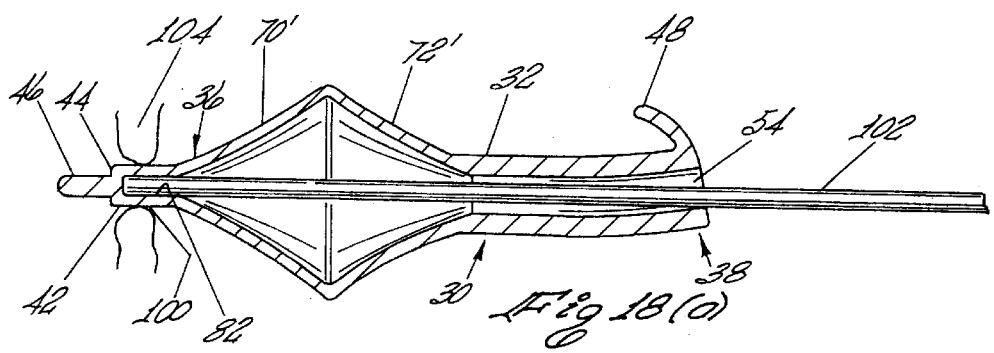
FIGS. 18(a) through 18(d) illustrate pictorially the steps of a method for inserting the punctum plug illustrated in FIG. 17 through the punctum opening and the vertical portion of the canaliculus into the ampula of an eye.
Figure 18B:
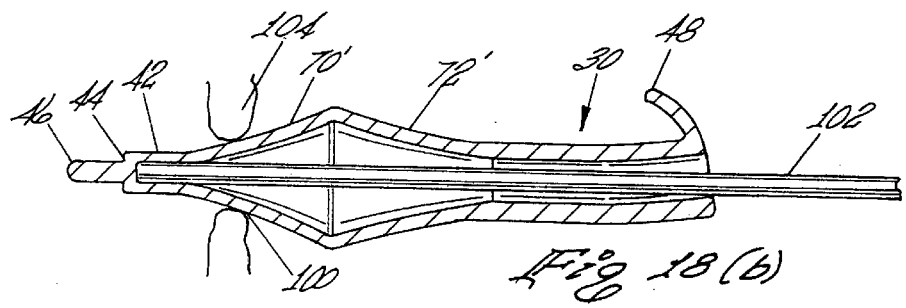
Figure 18C:
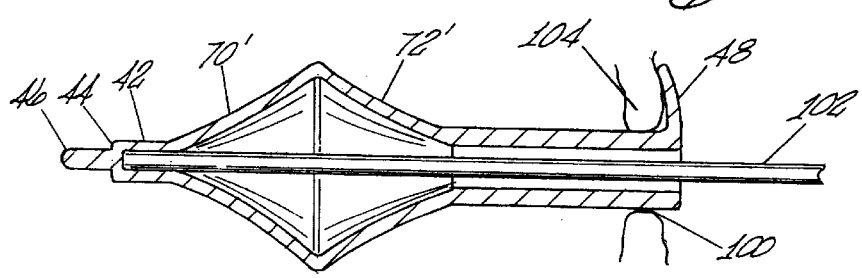
Figure 18D:
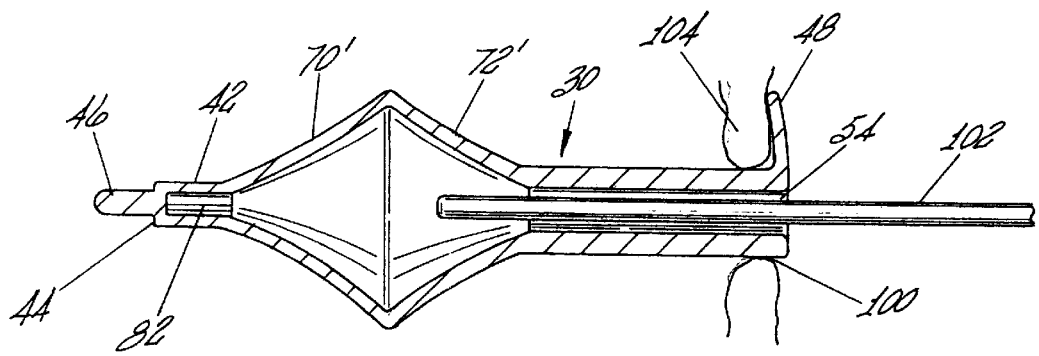

FIG. 17 shows a similar structure wherein the conical-shaped members 70' and 72' have curved outer walls.

The cross-sections of the embodiments illustrated in FIGS. 16 and 17 may be either circular or elliptically.

FIGS. 18(*a*), 18(*b*), 18(*c*) and 18(*d*) illustrate a method for inserting a punctum plug into the punctum opening 100 of an eye having a sphincter muscle illustrated as 104. The implant is to be transported through the punctum opening 100, through the vertical portion of a canaliculus and into the ampula to include the punctum opening 100. The implant includes elongated member 32 having a medial end 36 and a spaced, opposed lateral end 38 and a central member having a predetermined cross-sectional dimension extending from the medial end 36 to the lateral end 38. FIG. 18(*a*) illustrates that the distal starting tip 46 has expanded the punctum opening 100 enabling the tip insert section 42 to pass through the punctum opening 100 into the vertical portion of the canaliculus. The collapsible flared section 70' is illustrated about to be passed through the punctum opening 100. An insertion tool 102 is passed through the elongated opening 54 and into the tool receiving opening 82 to provide the insertion force at the medial end 36.

FIG. 18(*b*) illustrates that the collapsible flared section 70' has engaged the punctum opening 100 and the sphincter muscles 104 defining the side walls of the punctum opening 100 applies a force on the collapsible flared section 70' in a direction to collapse the same and to urge the collapsible flared section 70' from its extended position as illustrated in FIG. 18(*a*) to a collapsed position. As the punctum plug 30 is advanced through the punctum opening 100 and vertical portion of the canaliculus by the application of an insertion force on the insertion tool 102, the entire collapsible flared section 70' and 72', which is illustrated in FIG. 18(*b*) passed completely through the punctum opening 100.

FIG. 18(*c*) illustrates that when the collapsible flared sections 70' and 72' are passed through the punctum opening 100 through the vertical portion of the canaliculus into the ampula, the collapsible flared sections 70' and 72' then revert back to their substantially extended positions to occlude the punctum opening and the vertical portion of the canaliculus.

FIG. 18(*d*) illustrates the withdrawal of the insertion tool 102 from the inserted punctum plug 30. The thin elongated lip 48 is positioned to be located remotely from the cornea of the eye.

Figure 19:
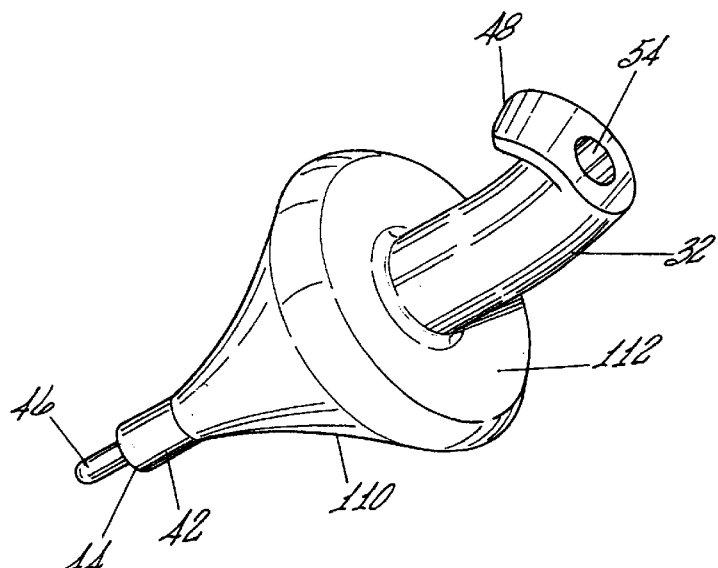
FIG. 19 is a perspective front bottom and right hand view of yet another embodiment of a punctum plug having a annular shaped balloon which defines the outer edge of a collapsible conical-shaped flared section.
Figure 20:
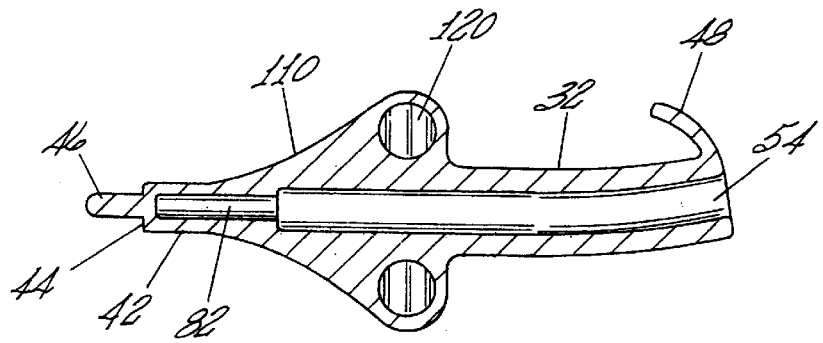
FIG. 20 is a cross sectional bottom elevational view of the punctum plug illustrated in FIG. 19 showing the position of the annular shaped balloon.

FIGS. 19 and 20 disclose yet another embodiment of an implant wherein the conical-flared section 110 is formed to have curved side walls and is formed of a resilient collapsible material. To facilitate the collapsing of the conical-shaped member which defines the collapsible flared section 110, an annular shaped balloon or opening 120 provides a collapsible space to enable the widest dimension of the implant to collapse as it is passed through the punctum opening and vertical portion of the canaliculus.

Figure 21:
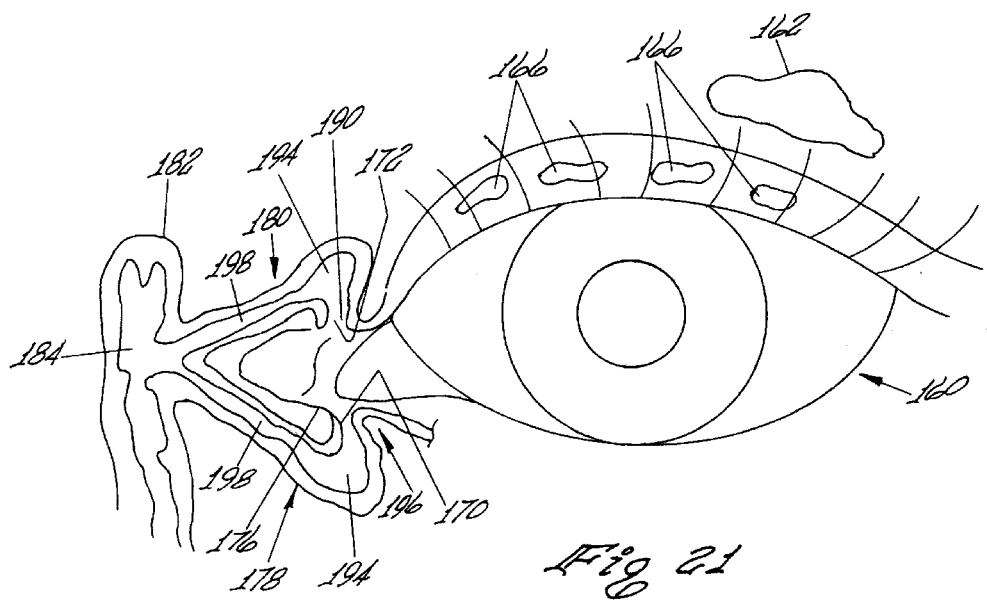
FIG. 21 is a pictorial representation of a lacrimal system of the eye having an upper and lower canaliculus, each of which have a punctum opening, vertical portion of the canaliculus, an ampula or sac and a horizontal portion of the canaliculus.

In order to better understand the teachings of the present invention, and the structure of the eye in its relationship to the present invention, the following brief description of the human eye and the associated lacrimal system illustrated in FIG. 21 and showing the paths of the tears from sources of the tears to the nasal cavity, will first be discussed.

The eye 160 includes a cornea and a pupil which is well known in the art. The source of the tears for the eye 160 is generally classified into "crying tears" and "constant tears". The "crying tears" are produced by a large lacrimal gland 162 illustrated in the upper right hand portion of the illustration of eye 160. The "constant tears" are produced by a series of small glands 166 which are located below the large gland 162 and spaced apart above the cornea of the eye 160. The "constant tears" are the tear secretions which are to be preserved in accordance with the teachings of the present invention.

In the normal eye, approximately 400 drops (9.5 milliliters) of tear secretion are produced during the day and a lesser volume of tear secretion is produced at night during sleep. Tear secretion also protects the eye from infection since the tears contain an enzyme called Lysozyme that functions as an antibiotic. With age, the eye produces less tear secretion, about sixty percent (60%) less at age 65 than at age 18. The tears flow over the eyes and drain through the small openings called the puncta, or punctal openings or punctum openings. There are two punctal openings in the eye, a lower punctum 170 and an upper punctum 172. The punctal openings 170 and 172 form openings into the corresponding a lower canaliculus 178 and an upper canaliculus 180. Each of the punctal openings 170 and 172 have the sphincter muscle, illustrated as muscle 176, formed therearound. The sphincter muscle 176 is a fairly dense relatively avascular connective ring of tissue. The lower canaliculus 178 and the upper canaliculus 180 are connected to a lacrimal sac 182. The lacrimal sac 182 is connected to a nasal lacrimal duct 184. The lacrimal duct 184, in turn, extends into the nasal cavity (not shown). The tears produced by the eye travel through the punctal openings, through their associated canaliculus.

As the tears exit the lower canaliculus 178 and the upper canaliculus 180, the tear flows merge in the lacrimal duct 184 and then travel to the nasal cavity. Lower canaliculus 178 and the upper canaliculus 180, which comprise the drainage channels of the eye travel to the nasal cavity. Lower canaliculus 178 and the upper canaliculus 180, which comprise the drainage channels of the eye travel to the nasal cavity. Lower canaliculus 178 and the upper canaliculus 180, which comprise the drainage channels of the eye are connected to an ampula or sac, shown generally as 194, which has a dimension of about 2 mm to 3 mm at its widest portion. The ampula or sac 194 narrows into the horizontal portion of the canaliculus, shown generally as 198. The medial position of the horizontal portion of the canaliculus, sometimes referred to as the horizontal canaliculus, has a diameter in the order of about 0.5 mm and an overall length of about 8 mm. In practicing the present invention, the punctum plug or implant is placed in the vertical portion 190 of the canaliculus 178 and 180.

It has developed that mechanism of lacrimal drainage results in the drainage of tear flow from the eye. One article which describes this phenomenon is entitled *"BLINKING AND THE MECHANICS OF THE LACRIMAL DRAINAGE SYSTEM"* by Marshall G. Doane, Ph.D., which appeared in OPHTHALMOLOGY, Volume 88, No. 8, August 1981, pages 844 through 851 inclusive (the "Doane Article"). The Doane Article describes that during each blink cycle, the upper lid sweeps down over the eye. As the lid descends, the papillae containing the punctal opening elevate from the medial lid margin. As the lid continues to descend, the puncta are occluded by the contact of the lid margins. Further lid closure squeezes the canaliculi and sac forcing the tear or contained fluid to drain into the nasolacrimal duct. At the end of a complete lid closure, the lacrimal system is compressed and largely empty of fluid. During the opening phase, the puncta are still occluded. The walls of the passage ways or canaliculus expand by elastic force causing a partial vacuum or suction. As the lid continue to open, the puncta "pop" apart, and excess tear fluid is immediately drawn off the eye into the canaliculus.

The insertion of an implant into the ampula of the canaliculus tends to retard the squeezing action of the canaliculi during eyelid closure and to reduce the partial vacuum during eyelid opening which results in a larger quantity of tear fluid remaining on the eye. If medication is added to the eye, it remains on the eye longer thereby effecting the eye treatment by the medication which, otherwise, would be removed by the blinking and the mechanics of the lacrimal drainage system.

In utilizing the punctum plug or implant for practicing the teaching of the invention, the eye surgeon can utilize any one of a number of methods for determining if an external condition due to a deficiency of tears exists. In the preferred embodiment of the present invention, the canaliculus can be temporarily occluded by placing a temporary implant (which may be a temporary punctum plug or canalicular implant) to provide a temporary blockage of the punctum opening or canaliculus as the case may be. By utilizing a temporary implant for providing temporary blockage, the eye surgeon can observe the response of the patient to the temporary blockade. If an improvement in the eye condition of the patient is noted, a permanent punctum plug or implant can be implanted within the punctum opening and vertical portion of the canaliculus or ampula of the patient.

It is envisioned that the temporary implant used in practicing the invention can be in the form of one of the embodiments described hereinbefore with respect to FIGS. 1 through 20 of the present invention. If a punctum plug or implant is to function as a temporary implant to provide temporary blockage of the punctum opening or vertical portion of the canaliculus, the temporary implant can be fabricated from a medically acceptable, dissolvable biodegradable material such as collagen, catgut, biodegradable suturing material, polyglycolic acid or the like. The temporary punctum plug or implant can be inserted into the punctum opening and vertical portion of the canaliculus and/or ampula utilizing the procedures set forth hereinbelow in FIGS. 22(*a*) through 22(*c*).

If the eye surgeon determines that a permanent occlusion of the punctum opening and vertical portion of the canaliculus is desirable, a permanent punctum plug or implant can be utilized as a means for providing a permanent occlusion of the punctum opening and the vertical portion of the canaliculus. In such event, the permanent punctum plug or implant can be fabricated from a non-biodegradable material or material and one which is not absorbable by or dissolved in the human body. Examples of such materials are medical grade rubber, silicone, polyethylene, polypropylene, polytetrafluoroethylene (e.g. Teflon) are some of the materials. The diameter of the elongated member of the punctum plug would be in the order of about 0.2 mm to about 1.2 mm and the overall length could be in the order of about 1 mm to about 3 mm. The preferred diameter for elongated member of the punctum plug is in the order of about 0.5 mm to about 1.0 mm.

Figure 22A:
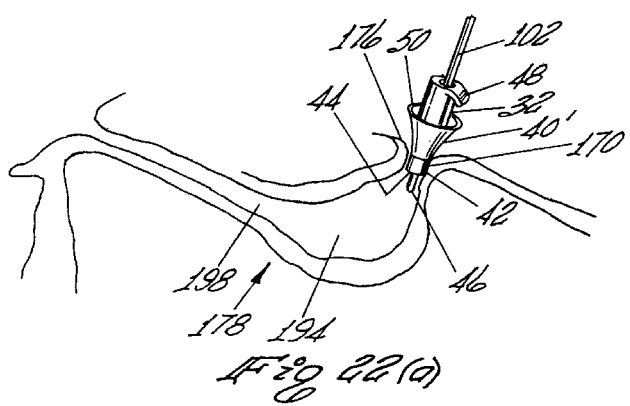

Referring now to the pictorial representations of FIGS. 22(*a*) through 22(*c*). FIGS. 22(*a*) through 22(*c*) illustrate the method for inserting the punctum plug into the punctum opening and vertical portion of the canaliculus of the eye. In FIGS. 22(*a*) through 22(*c*), the pictorial representations are shown based upon the punctum plug 30 being inserted into the punctum opening, and into the vertical portion of the lower canaliculus 78. If desired, as shown in FIGS. 22(*c*) and 23, the length of the punctum plug can be selected to place the collapsible flared section into the ampula 194. Of course, the punctum plug 30 could be inserted into the upper canaliculus 180 in a similar manner as described below. As illustrated in FIG. 22(*a*), an insertion tool 102 is inserted into the elongated opening 54 of the central member 32 and extends into the collapsible flared section 40' of the punctum plug and cooperates with the central section thereof such that the distal end or tip of the insertion tool 102 is positioned below the outer edge 50 defined by the thin-walled, conical-shaped member of the collapsible flared section 40'. The punctum plug 30 is positioned with the distal starting tip 46 of the tip insert section 44 located on the medial end 36 penetrating the punctal opening 170 such that the medial tip 36 will gently expand the sphincter muscle 176 defining the punctal opening 170. The collapsible flared section 40' is then passed through the punctal opening 170 until the punctal opening engages the exterior surface of the collapsible flared section 40'.

Figure 22B:
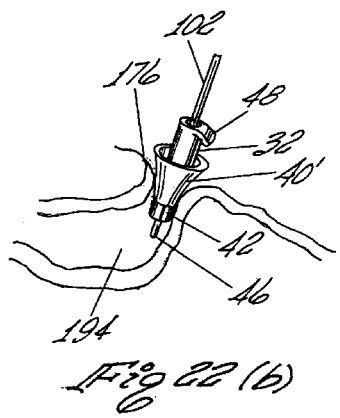

FIG. 22(b) illustrates that the sphincter muscle 176 slightly engages the collapsible flared section 40' as an insertion force is applied to the punctum plug 30 by the insertion tool 102. A radial force is applied around the surface of the collapsible flared section 40' as the punctum plug 30 slideably moves past the sphincter muscle 176. The sphincter muscle 176 applies a radial force to the collapsible flared section 40' in a direction so as to cause the collapsible flared section to be urged into its collapsed position. A clamping force is developed between the outer walls of the collapsed conical-shaped member defining the collapsible flared section 40' and the inner walls of the vertical section of the canaliculus holding the implant in place.

Figure 22C:
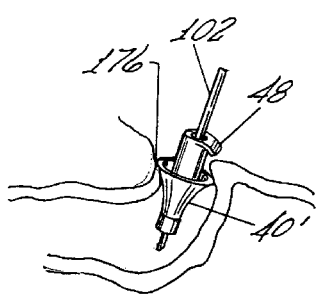

If the punctum plug is selected to have sufficient length to be inserted past the vertical portion of the canaliculus, then FIG. 22(c) illustrates that the insertion tool 102 continually applies an insertion force transporting the punctum plug 30 through the vertical portion of the canaliculus 190 and into the ampula 194. Due to the increased diameter of the ampula, the radial force is no longer applied against the collapsible flared section 40' and the collapsible flared section 40' that reverts back to its substantially extended position to occlude the punctum opening and the vertical portion of at least one canaliculi.

Figure 23:
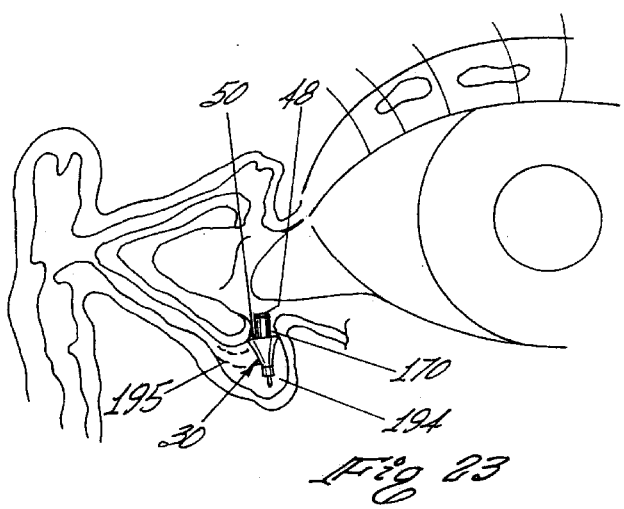
FIG. 23 is an pictorial representation showing that the collapsible flared section of the punctum plug reverts back to its substantially extended position when the same is positioned within the ampula and which occludes the punctum opening and vertical portion of the canaliculus.

This is illustrated in great detail in FIG. 23 wherein the angular curve between the medial end and lateral end is evident. The size, uniformity or non-uniformity of the punctum plug can be selected to provide the best conformity between the collapsible flared section and the size and shape of the interior of the ampula 190. For example, an elliptically shaped collapsible flared section as illustrated in FIGS. 12 through 15 may be the best punctum plug to provide occlusion of the punctum opening and vertical portion of the canaliculus than other embodiments illustrated herein. In such event, it would be preferable to use such a punctum plug having a non-uniform shape in lieu of a collapsible flared section having a uniform shaped and/or generally circular cross-section. If a punctum plug having a length in the order of 5 mm is used, dashed lines 195 illustrate the orientation of the medial end of the punctum plug.

In the alternative, a punctum plug having a structure illustrated in FIG. 10 with a bias outer edge 66 may hold better in the ampula, depending on the physical size and shape thereof. It is envisioned that an image could be made of the punctum opening, that portion of the canaliculus extending between the punctum opening and ampula and ampula size and shape and that the physical size, shape including the length of the elongated member 32 be selected to best fit the geometry of the eye.

Figure 24:
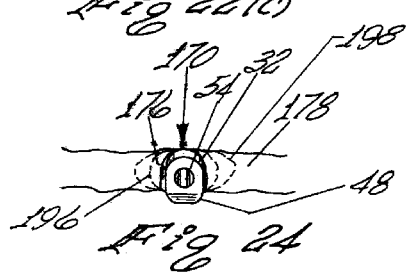
FIG. 24 is an enlarged pictorial representation of the thin elongated retaining lip in contact with the sphincter muscle defining the punctum opening with the retaining lip being positioned away from the cornea.

FIG. 24 illustrates pictorially the location of the thin elongated lip 48 over the edge of the punctum opening 170 which is defined by the sphincter muscle 176 in the lower eyelid 178. Due to the angular curvature of the second end relative to the first end, the thin elongated lip 48 and the first end of the central body are urged away from the cornea and engages the sphincter muscle 176. The punctum plug 30 is held in place by the action of the collapsible flared section 40' and the thin elongated lip 48. If the collapsible flared section is located in the ampula 194 as shown in FIG. 23, then the outer edge 50 cooperates with the ampula to hold the second end of the punctum plug in place and the thin elongated lip 48 holds the first end of the punctum plug in place to prevent migration thereof. Also, FIG. 24 has a dashed outline 196 illustrating diagrammatically a collapsible flared section having a generally circular cross-section and a dashed outline 198 illustrating diagrammatically a collapsible flared section having a generally elliptical cross-section.

If the collapsible flared section is located in the punctum opening and the vertical portion of the canaliculus, a clamping force is developed to hold the medial end of the punctum plug in place and the thin elongated lip 48 holds the lateral end of the punctum plug in place to prevent migration thereof.

By utilizing the teachings of the present invention, a method for treating external eye conditions due to a deficiency of tears is disclosed. The method includes the steps of testing the eye to determine if a tear deficiency exists; and, if a tear deficiency is determined, placing a punctum plug having an elongated member, a first end and a second end wherein the first end has a thin elongated lip and a second end having a collapsible flared section, within the punctum opening and that portion of at least one of the canaliculi located between the punctum opening and ampula.

The present invention also teaches a method for surgically inserting an implant through a punctum opening into the vertical portion of at least one of the canaliculi having interior side walls of an eye for treating external eye condition due to a deficiency of tears. The method comprises the steps of inserting a punctum plug having an elongated central member and a pair of ends wherein one end of said pair of ends has a collapsible flared section terminating in a starting tip and the other of said pair of ends has a thin elongated lip and wherein the starting tip and collapsible flared section pass through the punctum opening and into the vertical portion of at least one of the canaliculi interior of the eye causing the collapsed flared section to be collapsed as it passes through the punctum opening and vertical portion of the canaliculi and to return to its extended position within the ampula located adjacent to the vertical portion of said at least one canaliculi to occlude the punctum opening and the vertical portion of the canaliculus.

The step of urging in the above described method can include using a tool which is inserted into the central body to apply force to urge the punctum plug through the punctum opening, through the vertical section of at least one of the canaliculi and into the ampula.

The punctum plug or implant of the present invention utilizes the collapsible flared section as a means for occluding the punctum opening and the vertical portion of a canaliculi if a short elongated member is used. In such event, the collapsible flared section will remain in a collapsed position and a clamping force is developed between the collapsible flared section and the interior walls of the vertical portion of the canaliculus to hold the punctum plug in place.

If the length of the punctum plug is selected to extend the collapsible flared section into the ampula, the force which collapses the collapsible flared section is no longer present and the collapsible flared section then reverts back into its substantially extended position.

The punctum plug of the present invention is preferably used as a permanent implant for practicing the invention.

However, the temporary implant could, likewise, be a punctum plug or implant having a structure disclosed herein wherein the implant is formed of an absorbable or dissolvable (in the body) biodegradable material. The permanent punctum plug or implant can be identical in shape, size and dimension but be formed of a non-biodegradable, nonabsorbable or non-dissolvable (in the body) material. The advantage of utilizing a temporary implant and a permanent implant which has a structure as disclosed herein is that the collapsible flared section of the canalicular implant performs the function of occluding the punctum opening and/or the vertical section of the canaliculus. If the punctum plug does not extend all the way into the ampula and remains within the punctum opening and the vertical portion of the canaliculus, the collapsible flared section develops a clamping pressure between the collapsible flared section and the interior walls of the punctum opening or the vertical portion of the canaliculus while providing the desired blockage to the eye.

If it is desirable to have a small passageway available to enable a limited flow of tears to pass through the occlusion, it is envisioned that the punctum plug or implant could have an aperture extending axially through the central body thereof. For example, the punctum plug could have a lacrimal fluid control opening such as shown by opening 62 in FIGS. 8 and 9, to provide a passageway of a predetermined diameter to control tear secretion flow or, the alternative, a slot could be formed around the periphery thereof to facilitate a partial tear flow.

FIG. 25(a) illustrates a starting tip of a prior art lacrimal plug 200 wherein the tip is defined by a slope of about 45° and the starting tip is coaxial with the elongated axis of the elongated body. FIG. 25(b) illustrates a prior art implant 202 with out a starting tip. Typically, it is necessary to dilate the punctum opening to insert the implant.

FIG. 25(c) illustrates another embodiment of an implant 204 having a prior art starting tip having a rounded terminus. FIG. 25(d) illustrates another embodiment of an implant 206 having a prior art starting tip wherein a shoulder is formed around the distal end of the implant and a starting tip which is coaxial with the elongated axis of the elongated body is in the form of a rounded terminus. FIG. 25(e) illustrates an implant 208 having a "barbed shaped" insertion tip. FIG. 25(f) illustrates another embodiment of an implant 210 having a prior art starting tip wherein the slope is in the order of 8° to 10° to enable the starting tip to dilate the punctum opening.

As is evident from the above described implants having prior art starting tips, all of the starting tips are co-axially aligned with the elongated axis of the elongated body and have a geometrical dimension which is substantially equal to the geometrical dimension of the elongated body except for the prior art starting tip in FIG. 25(e) which is illustrated as the "barbed shaped" tip having a discrete shoulder formed therearound which causes the fibrous tissue defining the punctum opening to "snap back" to its original dimension after passing the "barbed shaped" tip.

As is evidenced from the implants having the prior art starting tips as described in FIGS. 25(a) through 25(f), the prior art starting tips are required to dilate the punctum opening or to have the punctum opening first dilated prior to insertion of the implant.

The implants illustrated in FIGS. 26 through 32 disclose a novel, unique and improved starting tip for implants including both punctum plugs and lacrimal implants. Further, as illustrated in FIG. 33, the horizontal canaliculus in actuality terminates in a horizontal sac. A punctum opening and that portion of the canaliculus between the punctum opening and ampula pass to the punctum plug or lacrimal implant depending on where the desired location within the canaliculus to be used for occluding the canaliculus. Also, as illustrated in FIG. 33 a punctum plug remains in the punctum opening, in that portion of the canaliculus located between the punctum opening and the ampula and the distal insert section or shaped insert section extends into and is positioned within the ampula.

FIG. 26 illustrates an embodiment of an implant 220 having an elongated body 224 having an elongated central axis 226. The elongated body 224 terminates in starting tip having a sloping and offset shaped insert section 228. Shaped insert section 228 is offset from the elongated 226 and terminates in a pointed distal insertion tip 230.

FIG. 27 illustrates yet another embodiment of an implant 234 having an elongated body 238 having an elongated central axis 242. The elongated body 238 terminates in a starting tip having a shaped insertion section 244 having an enlarged annular shaped proximal section 248 and which has one side which has a greater slope towards a distal starting tip 232 which is co-axial and aligned with the elongated central axis 242 of the elongated body 238. The enlarged annular shaped proximal area 272 cooperates with the fibrous tissue defining the punctum opening to controllably first expand the punctum opening and then to controllably permit the punctum opening to return to its original shape.

FIG. 28 illustrates still yet another embodiment of an implant 258 having an elongated body 262 having an elongated central axis 264. The elongated body 262 which terminates in a starting tip having a shaped insertion section 266 having enlarged annular shaped proximal area 272 defining a circumferentially extending outer edge 276 which has one side which has a greater slope towards a distal starting tip 280 which is co-axial and aligned with the elongated axis 264 of the elongated body 262. The enlarged annular shaped proximal area 272 cooperates with the fibrous tissue defining the punctum opening to controllably first expand the punctum opening and then to controllably permit the punctum opening to return to its original shape.

FIG. 29 illustrates another embodiment of an implant 284 having an elongated body 288 having an elongated central axis 290. The elongated body 288 terminates in starting tip having a partially curved and sloped surface shaped insert section 292 wherein the partially curved and sloped surface is arcuate shaped as shown by surface 294 and which terminates in a distal starting tip 296. Shaped insert section 292 is offset from the elongated axis 290 and terminates in the pointed distal insertion tip 296.

In FIGS. 30(a), 30(b) and 30(c), the implant illustrated as 300 is adapted to pass through a punctum opening illustrated as 302. As illustrated in FIG. 30(a), the distal starting tip 304 has a 30° slope defining a distal tip 306. Distal tip 306 is offset relative to the elongated axis of the elongated body, as described in FIG. 26. Because of the small acute angles slope of 30°, the distal tip 306 easily passes through the punctum opening 302. A 30° slope would be used for punctum openings that are in the small to mid-range of the typical punctum opening sizes.

As illustrated in FIG. 30(b), the distal starting tip 304' has a 40° slope defining a distal tip 306'. Distal tip 306' is offset relative to the elongated axis of the elongated body, as described in FIG. 26. Because of the small acute angles slope of 40°, the distal tip 306' easily passes through the punctum opening 302. A 40° slope would be used for punctum openings that are in the mid-range of the typical punctum opening sizes.

As illustrated in FIG. 30(c), the distal starting tip 304" has a 45° slope defining a distal tip 306". Distal tip 306" is offset relative to the elongated axis of the elongated body, as described in FIG. 26. Because of the small acute angles slope of 45°, the distal tip 306" easily passes through the punctum opening 302. A 45° slope would be used for punctum openings that are in the mid-range to large of the typical punctum opening sizes.

In operation, as illustrated in FIG. 30(a) the sloped surface 310 engages the fibrous tissue of the punctum opening 302 applying a downward pressure thereon which tends to elongate the punctum opening into a somewhat oval shape which is different than the dilation action of the prior art starting tip which tend to uniformly expand the entire punctum opening. By elongating the punctum opening into an oval shape, rather than uniformly expanding the entire periphery of the punctum opening which is typical of the prior art starting tips, there is less trauma on the punctum opening.

FIG. 31 illustrates an implant 310, which is a modification of the implant 220 illustrated in FIG. 26, wherein the elongated body 314 has elongated axis through 316 which terminates in a starting tip 320 having an offset and indented partially curved and sloped surface 322 which terminates in a distal starting tip 326 and wherein the distal starting tip 326 is offset relative to the elongated central axis 316 of the elongated body 314.

FIG. 32 illustrates an implant 332, which is a modification of the implant 220 illustrated in FIG. 26, wherein the elongated body 336 has elongated axis through 338 which terminates in a starting tip 342 having a rounded terminus 346 and wherein the distal starting tip 342 is offset relative to the elongated central axis 338 of the elongated body 336.

FIG. 33 illustrates, in a pictorial representation, the path traversed by an implant 300 illustrated in FIGS. 30(a), 30(b) and 30(c) when passed through the punctum opening 302 and into the horizontal canaliculus 360 including the horizontal sac 362. The implant shown by dashed line 300' illustrates the position of the implant after the implant has passed through the punctal opening 302 and a horizontal sac 362. It is apparent that by positioning the shaped insert section 304 at an opposed location relative to the opening into the horizontal canaliculus 360 the shaped insertion section 304 easily bides the implant 300 in the horizontal canaliculus 360. Again, the sloped surface 310 tends to elongate or stretch the horizontal canaliculus into an oval shape which permits the implant to engage and be held in position by the inner walls of the horizontal canaliculus 360.

FIGS. 34(a), 34(b), 34(c) and 34(d) illustrates the steps of a method for inserting an implant 300, as illustrated in FIG. 30(a) wherein the offset starting tip 306 is used to slightly dilate the punctum opening into an oval shape during insertion. FIG. 34(a) illustrates that the distal starting tip 306 is passed as close as possible to the center of the punctum opening. In FIG. 24(a) the implant 300 is shown to have a diameter of about 0.3 mm and the punctum opening is shown to have a diameter of about 0.3 mm.

FIG. 34(b) illustrates the location of the distal starting tip 306 just before the sloped surface 310 engages the inner edge of the fibrous tissue defining the punctum opening.

FIG. 34(c) illustrates that the sloped edge 310 of the implant 300 has urged the punctum opening 302 into a slightly elongated shape to pass the implant 300. FIG. 34(d) illustrates diagrammatically that the lines of force applied to the punctum opening 302 are illustrated by arrows 370 and 372 the force illustrated by arrow 372 tends to cause the fibrous tissue slideably engaged therewith to elongate into an oval shape due to the relative force differential between the forces illustrated by arrows 370 and 372.

It is also envisioned that the punctum plug or implant of the present invention could include material which is responsive to actinic radiation, such as for example X-rays, so that the eye surgeon can perform tests to determine if the punctum plug or implant is properly located within the punctum opening and vertical section of the canaliculus. One such material that can be utilized is barium, in appropriate concentrations known to persons skilled in the art, so as to be responsive to actinic radiation, such as X-rays. The use of such materials responsive to actinic radiation is of such a low enough level that it does not cause any adverse effects to the patient into which a punctum plug or implant containing the same is implanted.

Typical dimensions for the punctum plug may include the elongated member having a diameter of about 0.5 mm to about 1.2 mm. The diameter of the outer ring defining the outer edge of the collapsible flared section may be in the order of about 1.5 mm to about 2.5 mm. The overall length of the implant could be about 2 mm to about 5 mm.

The diameter of the distal starting tip can be about 0.2 mm to about 0.4 mm with about 0.3 mm being preferred.

What is claimed is:

1. An implant comprising
    an elongated member having a pair of ends and an outer surface wherein one of said pair of ends includes a thin elongated lip which protrudes beyond the outer surface of the elongated member and is located approximately 300 degrees or less of the periphery of the elongated member leaving a posterior surface free from protruding into or from contacting with or abrading a surface of the eye including the cornea or conjunctiva, said thin elongated lip being located on said elongated member to position the thin elongated lip in a generally anterior direction upon insertion in to a punctum opening to position the posterior surface away from a surface of an eye, said elongated member being formed of a dimension to pass through a punctum opening of an eye.

2. The implant of claim 1 wherein said elongated member has an elongated axis and wherein said thin elongated lip has a posterior surface and central axis wherein said central axis is positioned anterior to the elongated axis of said elongated member and positions the posterior surface away from a surface of an eye.

3. The implant of claim 1 wherein said elongated member has an elongated axis and wherein said thin elongated lip has a central axis and having a portion of the posterior surface removed adjacent the central axis and wherein said central axis is co-axial and aligned with the elongated axis of said elongated member to position the posterior surface away from a surface of an eye.

4. The implant of claim 2 wherein said one of said pair of ends of said elongated member is curved anteriorly relative to the thin elongated lip.

5. An implant comprising
    an elongated member having a pair of ends and an outer surface wherein one of said pair of ends includes an external retaining member which protrudes beyond the outer surface of the elongated member and is located approximately 300 degrees or less of the periphery of the elongated member leaving a posterior surface free from protruding into or from contacting with or abrading a surface of the eye including the cornea or conjunctiva and wherein said elongated member has a portion curved anteriorly relative to said external retaining member, said external retaining member being located on said elongated member to be positioned adjacent to said curved portion and in a generally anterior direction upon insertion into a punctum opening to position the posterior surface away from a surface of an eye, said elongated member being formed of a dimension to pass through a punctum opening of an eye.

6. An implant comprising an elongated member having a pair of ends and an outer surface wherein one of said pair of ends includes a collapsible flared section having an outer surface and the other of said pair of ends includes a thin elongated lip which protrudes beyond the outer surface of the elongated member and is located approximately 300 degrees or less of the periphery of the elongated member leaving a posterior surface free from protruding into or from contacting with or abrading a surface of the eye including the cornea or conjunctiva and wherein said elongated member is shaped to position the posterior surface away from a surface of an eye, said elongated member and said collapsible flared section being formed of a dimension to pass through a punctum opening of an eye.

7. The implant of claim 6 wherein the elongated member curves slightly in a direction towards said other of said pair of ends.

8. The implant of claim 6 wherein said elongated member has a central axis and wherein said collapsible flared section is collapsible relative to said central axis in response to the application of a force on the collapsible flared section in a direction to collapse the collapsible flared section and to urge the collapsible flared section into a collapsed position.

9. The implant of claim 6 having a fluid control opening extending therethrough to pass lacrimal fluid.

10. The implant of claim 9 wherein said fluid control opening is selected to have a predetermined diameter to control the flow of lacrimal fluid passed therethrough.

11. The implant of claim 10 wherein said fluid control opening has a diameter in the range of about 0.10 mm to about 0.40 mm.

12. A punctum plug comprising an elongated central member having a central axis and a pair of ends and an outer surface wherein one of said pair of ends includes means defining a collapsible flared section terminating in a starting tip which is capable of dilating a punctum opening by urging the punctum opening into a substantially oval shape and wherein said collapsible flared section is capable of being collapsed relative to said central axis in response to the application of force on the collapsible flared section in a direction to collapse the collapsible flared section and the other of said pair of ends includes a thin lip which protrudes beyond the outer surface of the elongated member and is located approximately 300 degrees or less of the periphery of the elongated member leaving a posterior surface free from protruding into or from contacting with or abrading a surface of the eye including the cornea or conjunctiva and wherein said elongated central member is shaped to position the posterior surface away from a surface of an eye, said elongated central member and said collapsible flared section being formed of a dimension to pass through a punctum of an eye.

13. The implant of claim 12 wherein said starting tip includes a tip insert section having predetermined cross-sectional dimension and wherein the tip insert section has an offset distal starting tip which is smaller in cross-sectional dimension than said tip insert section.

14. The implant of claim 12 wherein said tip insert section has a sloped surface.

15. The implant of claim 12 wherein said collapsible flared section has an initial cross-sectional dimension at said second end which is substantially equal to said predetermined cross-sectional dimension and which increases in cross-sectional dimension as said collapsible flared section extends towards said first end.

16. The implant of claim 15 wherein said collapsible flared section terminates in an outer edge.

17. The implant of claim 16 wherein said collapsible flared section and outer edge are elliptically shaped and said collapsible flared section is responsive to a force applied in direction to collapse the collapsible flared section and to urge the collapsible flared section into a collapsed position.

18. An implant comprising an elongated member having a pair of ends and an outer surface wherein one of said pair of ends includes a shaped distal tip forming a starting tip having an outer surface and the other of said pair of ends includes a thin elongated lip which protrudes beyond the outer surface of the elongated member and is located approximately 300 degrees or less of the periphery of the elongated member leaving a posterior surface free from protruding into or from contacting with or abrading a surface of the eye including the cornea or conjunctiva, said thin elongated lip being located on said elongated member to position the thin elongated lip in a generally anterior direction upon insertion in to a punctum opening to position the posterior surface away from a surface of an eye, said elongated member and said shaped distal tip being formed of a dimension to pass through a punctum opening of an eye.

19. The implant of claim 18 wherein said shaped distal tip is in the form of a collapsible flared section located between the starting tip and said thin elongated lip.

20. An implant comprising an elongated member having a pair of ends wherein one of said pair of ends terminates in a tip insertion section having a distal starting tip having a cross-sectional dimension that penetrates a punctal opening defined by a fibrous tissue and wherein said distal starting tip has a selected length to pass through the punctal opening to enable the tip insertion section to gently expand the sphincter muscle defining the punctum opening into a generally oval shape.

21. A punctum plug comprising an elongated member having a central axis, first end, a second end and a central section extending between said first end and said second end;

said elongated member having a slight angular curve which deflects said first end in a selected angle from said second end, said first end having a thin retaining lip; and said second end having said starting tip includes a tip insert section having predetermined cross-sectional dimension and wherein the tip insert section has an offset distal starting tip which is smaller in cross-sectional dimension than said tip insert section.

22. The implant of claim 21 wherein the second end terminates in a tip insertion section having a distal starting tip.

23. The implant of claim 22 wherein the diameter of the distal starting tip is about 0.2 mm to about 0.4 mm.

24. The implant of claim 21 wherein the diameter of the distal starting tip is about 0.3 mm.

25. The implant of claim 24 wherein the implant is formed of a biodegradable material.

26. The implant of claim 21 wherein the biodegradable material is a collagen material.

27. The implant of claim 21 wherein the implant is formed of a non-biodegradable material.

28. The implant of claim 21 wherein the non-biodegradable material is a silicone material.

29. An implant adapted to be inserted into the punctum opening of an eye to occlude the punctum opening, said implant comprising
   an elongated member having a first end and a spaced, opposed second end and a central member having a predetermined cross-sectional dimension extending from said first end to said second end;
   said first end having a starting tip including a tip insert section having predetermined cross-sectional dimension and wherein the tip insert section has an offset distal starting tip which is smaller in cross-sectional dimension than said tip insert section; and
   said second end including a thin elongated lip which is located on said elongated member and which protrudes beyond the outer surface of the elongated member and is located approximately 300 degrees or less of the periphery of the elongated member leaving a posterior surface free from protruding into or from contacting with or abrading a surface of the eye including the cornea or conjunctiva to position the thin elongated lip in a generally anterior direction upon insertion in to a punctum opening and which is adapted to engage the punctum opening.

30. The implant of claim 29 wherein the elongated member has a slightly angular curve in a selected direction causing the second end to be slightly deflected relative to the first end for urging the thin elongated lip into holding engagement with the punctum opening.

31. A method for treating an external eye condition due to a deficiency of tears including the steps of
   testing the eye to determine if a tear deficiency exists; and
   if a tear deficiency is determined to exist, inserting into the punctum opening an implant having an elongated central member and a pair of ends and an outer surface wherein one end of said pair of ends has a starting tip and wherein said starting tip includes a tip insert section having predetermined cross-sectional dimension and has an offset distal starting tip which is smaller in cross-sectional dimension than said tip insert section and the other of said pair of ends has a thin elongated lip being located on said elongated member which protrudes beyond the outer surface of the elongated member and is located approximately 300 degrees or less of the periphery of the elongated member leaving a posterior surface free from protruding into or from contacting with or abrading a surface of the eye including the cornea or conjunctiva to position the thin elongated lip in a generally anterior direction upon insertion in to a punctum opening wherein the starting tip dilates and passes through the punctum opening and into the canaliculi interior of an eye to occlude the punctum opening and the vertical portion of the canaliculus.

32. The method of claim 31 further comprising the step of positioning the lip over the punctum opening to hold the implant in place between the punctum opening and the ampula.

33. A punctum plug comprising
   an elongated central member having a central axis and a pair of ends wherein one of said pair of ends includes an enlarged collapsible annular shaped section terminating in a starting tip wherein said starting tip is inserted into and dilates the punctal opening for receiving and passing said enlarged annular shaped section through the dilated punctual opening, said elongated central member and said enlarged annular shaped section being formed of a dimension to pass through a punctual of an eye, and wherein the other of said pair of ends has a lip for engaging the punctum opening and positioning said enlarged annular shared section in a canaliculus adjacent a punctual of an eye.

34. The punctum plug of claim 33 wherein said opening and the other of said pair of ends includes an external retaining member.

35. The punctum plug of claim 33 wherein said enlarged annular shaped section is in the form of a relatively rigid flared section.

36. The punctum plug of claim 33 wherein said enlarged annular shaped section is in the form of a conical shaped flared section.

37. The punctum plug of claim 33 wherein said enlarged annular shaped section is conical shaped having a rounded outer edge to facilitate passage of said enlarged annular shaped section through the dilated punctum opening.

38. The punctum plug of claim 33 wherein said enlarged annular shaped section has one side which has a greater slope towards said starting tip.

39. An implant comprising
   an elongated member having a pair of ends wherein one of said pair of ends includes a shaped distal tip forming a starting tip having an outer surface and the other of said pair of ends includes a thin elongated lip having a posterior surface and wherein said shaped distal tip is in the form of a collapsible flared section located between the starting tip and said thin elongated lip, said thin elongated lip being located on said elongated member to position the thin elongated lip in a generally anterior direction upon insertion in to a punctum opening to position the posterior surface away from a surface of an eye, said elongated member and said shaped distal tip being formed of a dimension to pass through a punctum opening of an eye.

40. An implant adapted to be inserted into the punctum opening of an eye to occlude the punctum opening, said implant comprising
   an elongated member having a first end and a spaced, opposed second end and a central member having a predetermined cross-sectional dimension extending from said first end to said second end;
   said first end having a starting tip including a tip insert section having predetermined cross-sectional dimension and wherein the tip insert section has an offset distal starting tip which is smaller in cross-sectional dimension than said tip insert section; and
   said second end including a thin elongated lip which is located on said elongated member to position the thin elongated lip in a generally anterior direction upon insertion in to a punctum opening and which is adapted to engage the punctum opening, said elongated member having a slightly angular curve in a selected direction causing the second end to be slightly deflected relative to the first end for urging the thin elongated lip into holding engagement with the punctum opening.

41. A punctum plug comprising
   an elongated central member having a central axis and a pair of ends wherein one of said pair of ends includes an enlarged annular shaped section terminating in a starting tip and has one side which has a greater slope towards said starting tip and wherein said starting tip is inserted into and dilates the punctal opening for receiving and passing said enlarged annular shaped section through the dilated punctual opening, said elongated central member and said enlarged annular shaped section being formed of a dimension to pass through a punctual of an eye.

42. A lacrimal occluder comprising an elongated member having a pair of ends wherein one of said pair of ends terminates in a tip insertion section in the form of a collapsible flared section and having a distal starting tip having a cross-sectional dimension that penetrates a punctal opening defined by a fibrous tissue and wherein said distal starting tip has a selected length to pass through the punctal opening to enable the tip insertion section to gently expand the sphincter muscle defining the punctum opening to a dimension and shape sufficient for passing the tip insertion section.

43. The lacrimal occluder of claim 42 wherein said collapsible flared section is conical shaped.

* * * * *